(12) United States Patent
Bhatia

(10) Patent No.: US 6,407,266 B2
(45) Date of Patent: Jun. 18, 2002

(54) CONTINUOUS PROCESS FOR THE MANUFACTURE OF ANHYDRO SUGAR ALCOHOLS AND REACTOR USEFUL THEREFOR

(75) Inventor: Kamlesh Kumar Bhatia, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/864,466

(22) Filed: May 24, 2001

Related U.S. Application Data

(60) Provisional application No. 60/207,313, filed on May 26, 2000.

(51) Int. Cl.$^7$ .......................................... C07D 493/04
(52) U.S. Cl. ...................................................... 549/464
(58) Field of Search ......................................... 549/464

(56) References Cited

U.S. PATENT DOCUMENTS

| | | | |
|---|---|---|---|
| 1,757,468 A | * | 5/1930 | Muller et al. ................ 549/464 |
| 3,454,603 A | | 7/1969 | Hartman |
| 4,169,152 A | | 9/1979 | LeMaistre et al. |
| 4,506,086 A | | 3/1985 | Salzburg et al. |
| 4,564,645 A | | 1/1986 | Salzburg et al. |
| 4,564,692 A | | 1/1986 | Feldmann et al. |
| 4,659,846 A | | 4/1987 | Maurer et al. |
| 6,288,284 B1 | | 9/2001 | Eek et al. |

FOREIGN PATENT DOCUMENTS

| | | |
|---|---|---|
| CA | 1178288 | 11/1984 |
| CA | 1195687 | 10/1985 |
| DD | 132266 | 9/1978 |
| DE | 3233086 A1 | 8/1984 |
| WO | 0014081 A | 3/2000 |

OTHER PUBLICATIONS

Montgomery et al, J. Chem. Soc., pp. 433–436 (1997).*
Hicks and Fraser–Reid, 1974, Can. J. Chem., 52: 3367–3672.
Defaye, Gadelle and Pedersen, 1990, Carbohydrate Research, 205: 191–202.
Montgomery and Wiggins, 1947, J. Chem. Soc., 433–436.
Fletcher, Jr., and Goepp, Jr., 1946, J. Am. Chem. Soc., 68(5):939–941.
Ropuszynski, Matyschok and Rzepka, 1969, Przem. Chem. 48(11):665–668.
Plucinski, Durda, and Sinicka, 1971, Pr. Nauk. Inst. Tech. Org. Tworz. Szxt. Pol. Wrocl., No. 3, 3–14.
Fleche and Huchette, 1986, Starch/Starke, 38: No. 1.S ,26–30.
Bock, Pedersen and Thogersen, 1981, Acta. Chem. Scand. B 35: 441–449.

* cited by examiner

*Primary Examiner*—Bernard Dentz

(57) ABSTRACT

This invention concerns a process for the manufacture of anhydro- and dianhydro-hexitols, pentitols, and tetritols by the dehydration of sugar alcohols (alditols) in the presence of a dehydration catalyst.

12 Claims, 2 Drawing Sheets

CONTINUOUS PROCESS FOR THE MANUFACTURE OF ANHYDRO SUGAR ALCOHOLS AND REACTOR USEFUL THEREFOR

This application claims benefit of Provisional Application 60/207,313 filed May 26, 2000.

FIELD OF THE INVENTION

This invention concerns a process for the manufacture of anhydro- and dianhydro-hexitols, pentitols, and tetritols by the dehydration of sugar alcohols (alditols) and an integral dehydration reactor for conducting said process.

TECHNICAL BACKGROUND OF THE INVENTION

Anhydro sugar alcohols, in particular derivatives of mannitol, iditol, and sorbitol, are known for their therapeutic uses and uses in food. At least one of these, isosorbide, 1,4:3,6-dianhydrosorbitol, is useful as a monomer used in the manufacture of polymers and copolymers, especially polyester polymers and copolymers. Isosorbide is a derivative of sorbitol, which can be derived from various natural resources. Sorbitol may be regarded as a renewable natural resource for the manufacture of polymers.

Anhydro sugar alcohols are known to be produced by dehydration of the corresponding sugar alcohols (or monoanhydro sugar alcohols) by the action of various dehydration catalysts, typically strong acid catalysts. Examples of these catalysts include sulfonated polystyrenes ($H^+$ form) (German Patent DE 3 041 673 C2; Canadian Patent Disclosure CA 1 178 288 A1); and various mineral acids, such as HCl (U.S. Pat. No. 4,169,152; German Patent Disclosure DE 3 233 086 A1), $H_3PO_4$ (East German Patent Disclosure DD 1 32 266; Can. J. Chem., 52 (19) 3362-72 (1974)), HF (International Patent Disclosure WO 89/00162 A; Carbohydr. Res. 205 (1990) 191-202) and $H_2SO_4$ (German Patent Disclosures DE 3 521 809 A1 and DE 3 229 412 A1).

These processes are often performed in the presence of a solvent. As solvents, water (CA 1 178 288 A1; European Patent Disclosure EP 0 052 295 B1) and organic solvents such as toluene or xylene (Przem. Chem. 48 (11) 665-8 (1969)) are known to be useful.

Batch processes for the preparation of dianhydro sugar alcohols by acid dehydration have been described in numerous patents and articles, for example, U.S. Pat. Nos. 3,454,603; 4,564,692; and 4,506,086; Canadian Patent 1178288; and articles J. Am. Chem. Soc., 68(5) pp. 939-941 (1946); J. Chem. Soc., pp. 433-436 (1947); Przem. Chem. 48(11) pp. 665-668 (1969); and Pr. Nauk. Inst. Technol. Org. Tworzyw Sztucznych Politech. Wroclaw. No. 3., p. 3-14 (1971).

In particular, a batch process for the formation of the dianhydro sugar alcohol isosorbide has been described in the literature as a two step process involving intramolecular dehydration of sorbitol to sorbitan (1,4-monoanhydrosorbitol), and further reaction of sorbitan to isosorbide (1,4:3,6-dianhydrosorbitol) in an acid catalyzed dehydration—cyclization. In this process, an aqueous solution of sorbitol is charged to a batch reactor. The temperature is increased to 130° C.–135° C. under vacuum (35 mm Hg) to remove the water. When the sorbitol melt is free of water, a catalyst, usually sulfuric acid, is added and the temperature and vacuum levels are maintained. The operable temperature range of the reaction is very narrow. Higher temperatures lead to decomposition and charring of the end product, while lower temperatures inhibit the reaction rate due to difficulties in removal of the water of reaction. This reaction produces isosorbide and a higher molecular weight by-product. The by-product is presumably produced by water elimination between two or more sorbitol molecules, but its exact nature is not clearly defined. See Starch/Starke (1986), 38(c), 26–30 and Roland Beck, Pharm. Mfg Inc. (1996), 97–100. Other monoanhydro by-products, 2,5-anhydro-L-iditol and 2,5-anhydro-D-mannitol, are also known to be produced under some reaction conditions (Acta. Chem. Scand. B 35, 441–449 (1981)).

International Patent Application WO 00/14081 describes a continuous process for producing anhydro sugar alcohols, especially isosorbide, comprising the steps of introducing at least one sugar alcohol or monoanhydro sugar alcohol into a reaction vessel; dehydrating the sugar alcohol or monoanhydro sugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel.

It is an object of the present invention to provide an improved continuous process for the manufacture of anhydro sugar alcohols, especially isosorbide, by the acid catalyzed dehydration of sugar alcohols at pressures ranging from atmospheric to moderately above atmospheric pressure and in the presence of an inert gas purge that facilitates large scale, economical production without the use of organic solvents in the dehydration process. Such a process improves product safety and reduces the process waste load.

SUMMARY OF THE INVENTION

Disclosed is a process for the preparation of a dianhydro sugar alcohol comprising the steps of:

a) introducing to the first stage of a multistage reactor a process stream comprising at least one sugar alcohol or monoanhydro sugar alcohol and, optionally, water;

b) intimately contacting said process stream with a counter current flow of an inert gas at elevated temperature to remove the bulk of any water present to yield a dewatered process stream;

c) intimately contacting said dewatered process stream with a dehydration catalyst in the presence of a counter current flow of an inert gas at elevated temperatures to remove water of reaction as formed; and d) removing the reaction product from the bottom of the reactor.

DETAILED DESCRIPTION OF THE INVENTION

Figure 1:
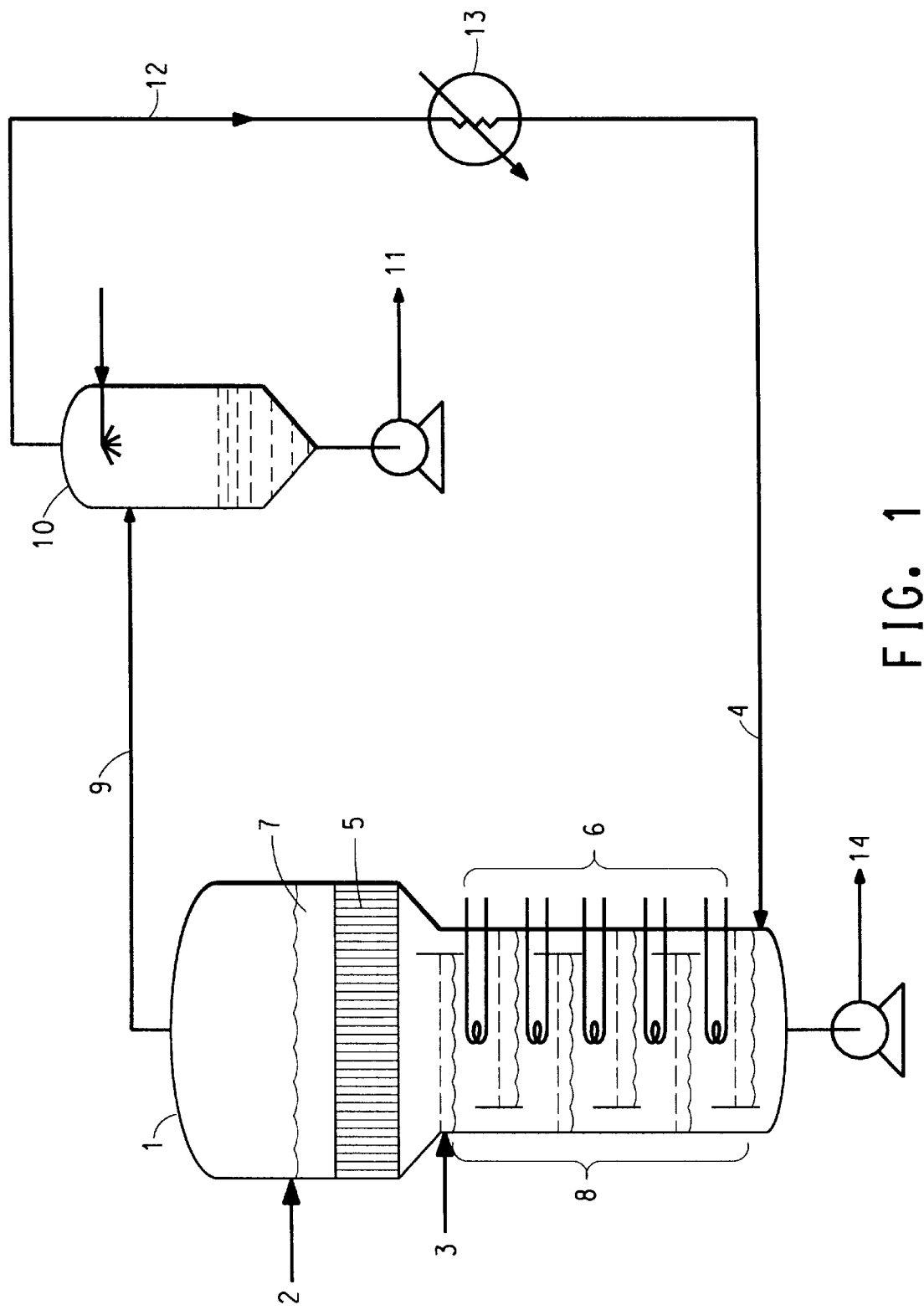
FIG. 1 is a schematic representation of a preferred embodiment of the process of the present invention.

The present disclosure describes a process for the production of anhydro and dianhydro sugar alcohols, most preferably, a process for the production of isosorbide, 1,4:3,6-dianhydrosorbitol.

The process is directed toward the production of anhydro sugar alcohols and generally includes the steps of introducing at least one sugar alcohol or monoanhydro sugar alcohol, usually in the form of an aqueous solution, into a vertical reaction vessel, in a downwardly flowing fashion, in the presence of a countercurrent flow of an inert gas; removing most of the water from said aqueous solution by evaporation; dehydrating the sugar alcohol or monoanhydro sugar alcohol in the presence of a catalyst to form a reaction product comprising anhydro sugar alcohol and water; removing the water of reaction from said reaction product by evaporation in the presence of a countercurrent flow of an inert gas; and removing the reaction product from the bottom of the reactor for subsequent use or purification.

Optionally, the process may further include one or more purification steps such as evaporation, distillation, extraction and ion-exchange or combinations thereof. Further, the process is preferably continuous such that the steps of introducing the starting sugar alcohol, removing water from the starting sugar alcohol, dehydrating the sugar alcohol, and removing the water of reaction, and removing product from the reactor occur simultaneously and the rates of reactant feed, and product removal are coordinated to maintain a steady amount of the reaction mass in the reactor.

Typical sugar alcohols, in particular tetritols, pentitols and hexitols, are suitable for use in the process as starting materials. The starting materials may be sugar alcohols, monoanhydro sugar alcohols, or a mixture thereof. Particularly preferred starting materials include erythritol, threitol, xylitol, arabinitol, ribitol, glucitol (also known as D-sorbitol or sorbitol), D-mannitol (mannitol), galactitol and iditol. The use of sorbitol is most preferred because sorbitol is readily available and can be obtained on a large industrial scale by the reduction of glucose with hydrogen, as known to one of ordinary skill in the art, and the resulting product, isosorbide, is especially valuable for use in the preparation of polyester polymers and copolymers. The preferred form of sorbitol is as its aqueous solution in water, available as an article of commerce as sorbitol, 70%, from Archer Daniels Midland, (Minneapolis, Minn.) or Cerestar or, Roquette Freres, Lestrem, France or in experimental quantities, from chemical supply houses such as Aldrich (Milwaukee, Wis.).

The catalysts used to facilitate the dehydration reaction are typically strong acid catalysts. Several types of acid catalysts may be used, each having specific advantages and disadvantages. One class of acid catalyst that may be used includes soluble acids. Examples of such acid catalysts include sulfuric acid, phosphoric acid, p-toluene sulfonic acid, methanesulfonic acid and the like. Sulfuric acid is a preferred catalyst from this class.

Alternatively, acid anion exchange resins may also be used, such as sulfonated polystyrenes, for example, AG50W-X12 from BioRad or perfluorinated ion-exchange polymers, such as Nafion®, available from E.I. du Pont de Nemours and Company (Wilmington, Del.). Inorganic ion exchange materials may also be used, such as acidic zeolites. In particular, H-beta zeolite from Degussa (Frankfurt, Germany) may be used in the process disclosed herein.

For the process of the present invention it is preferable to use a soluble catalyst and most preferable is the use of sulfuric acid. In this most preferable mode, sulfuric acid is used such that it comprises 0.25 to 2.5 wt % of the reaction mass, preferably 0.5 to 1.5 wt %. The sulfuric acid is supplied to the reactor as an aqueous solution ranging from 1 to 97% sulfuric acid. Acid strength is optimized such that the most concentrated solution of acid that results in no detrimental by-product formation at the point of introduction is used in order to reduce the overall water removal load on the reaction system.

The dehydration is performed at elevated temperatures between 100 and 180° C., preferably at temperatures between 115 and 160° C., and most preferably at temperatures between 115 and 145° C.

The dehydration is carried out by intimately contacting the reaction mass with a stream of counter currently flowing inert or non-reactive gas, preferably nitrogen or carbon dioxide, most preferably nitrogen. Preferably the nitrogen is recycled to the reactor system after cooling to reduce entrapped volatiles, predominantly water. The amount of nitrogen is typically between 0.5 to 1.5 lb per lb of sugar alcohol—water free basis. By "intimately contacting" is meant that the non-reactive gas, e.g. nitrogen, is injected into the system as a continuous stream of small bubbles so that effective contact with the reaction mass occurs.

The dehydration is preferably performed at approximately atmospheric pressure, although elevated or reduced pressures can also be used with minor adjustments to other process parameters, such as time and temperature. In one preferred embodiment, in commercial size equipment, there is a pressure gradient across a staged reaction ranging from approximately atmospheric to approximately 1.2 atmospheres pressure.

The dehydration catalyst (acid) addition can be performed in such a way that the catalyst is added in the requisite quantity initially, and further catalyst is added on an as-needed basis. However, it is also possible, and preferable, to add the catalyst in continuous fashion during the dehydration reaction.

The elevated temperature of the dehydration reaction promotes rapid dehydration of the starting materials. However, over-temperature, or prolonged high-temperature operation promote the formation of byproducts and/or the further conversion of the desired product to undesired secondary products over time. Therefore, it is desirable to remove the resultant reaction product from the high temperature reaction mixture rapidly to protect it against further reaction/decomposition. Preferably, the reaction product is drawn off from the reaction vessel continuously during the course of the dehydration reaction.

After dehydration of the starting material is completed, the acid catalyst may be deactivated and/or removed from the reaction product, which, preferably, has been removed from the reaction vessel. In the case of soluble acid catalysts, the deactivation may be accomplished by any method known in the art, such as addition of a metal hydroxide base to form an insoluble salt. Polymeric or inorganic ion exchange materials may be recovered by filtration.

Purification of the crude reaction product may occur by distillation, recrystallization, melt recrystallization or a combination thereof. A combination of distillation and recrystallization from an aliphatic alcohol such as methanol or ethanol may be employed in order to minimize the number of purification steps while maximizing the purity of the reaction product. This purification of the reaction product may occur as part of the continuous process or in a separate process. In either case, the purity of the resultant anhydrosugar alcohol should be at least 99.0%, preferably at least 99.5%, most preferably at least 99.8%, and preferably meets the purity requirements for use in polymer production.

A preferred process of the invention is described below in relation to FIG. 1.

As shown in FIG. 1, the dehydration takes place in a reaction vessel (1), which is provided with supply lines for the starting materials such as aqueous sugar alcohol solution (2), acid catalyst (3) and nitrogen (4). Vessel (1) is heated by means of heaters (5) and (6). Heater (5) supplies the majority of heat to the reactor and provides heat sufficient to remove the bulk of the water that enters the reactor with the feed of sorbitol 70% at (2). Any means of heat input at (5) can be used. A calandria is schematically represented. The heat input to heater (5) is adjusted to hold the temperature in the evaporation zone of the reactor (7) at approximately 120–130° C. Heaters (6) supply heat to the various dehydration stages of the reactor. Five dehydration stages (8), five heaters (6) are illustrated in FIG. 1. Input to the heaters (6) is adjusted to maintain the desired thermal gradient at the various dehydration stages of the reactor.

A flow of heated nitrogen (ca. 140° C.) enters the reactor at (4). The nitrogen contacts the descending reaction mass in a counter-current fashion, becomes essentially saturated with water-vapor, and exits the reactor overhead at (9). The temperature of this exiting flow of nitrogen approximates the temperature in the evaporation stage of the reactor (120–130° C.). The exit nitrogen is conducted to a condenser (10), a direct contact spray condenser is schematically represented, and the entrained water and any organics are removed from the nitrogen stream and sent to waste disposal (11). The cooled nitrogen stream (12) is conducted to a heater (13) where the nitrogen is heated back to process temperature prior to reintroduction to the reactor at (4). Product stream comprising 70–80% isosorbide with the balance comprising isosorbide oligomers, decomposition products and monoanhydro sorbitol derivatives exits the reactor at outlet (14).

In FIG. 1, five dehydration stages are illustrated. It is anticipated that the process of the present invention be conducted in one evaporation stage and one or more dehydration stages. The number of dehydration stages is preferably at least two, most preferably three to six. It is understood that the process of the present invention could also be carried out in more than one vessels connected so that the various vessels function as the stages of the reactor in FIG. 1.

The reactor of FIG. 1 is sized, and flow rates are adjusted such that hold up time for the sorbitol to isosorbide reaction mass is in the range of 1 to 3 hours, preferably 1.5 to 2.5 hours with the assumption that the temperature at the top of the reactor is 120–130° C. and the temperature of the exit stream is approximately 140–145° C.

Figure 2:
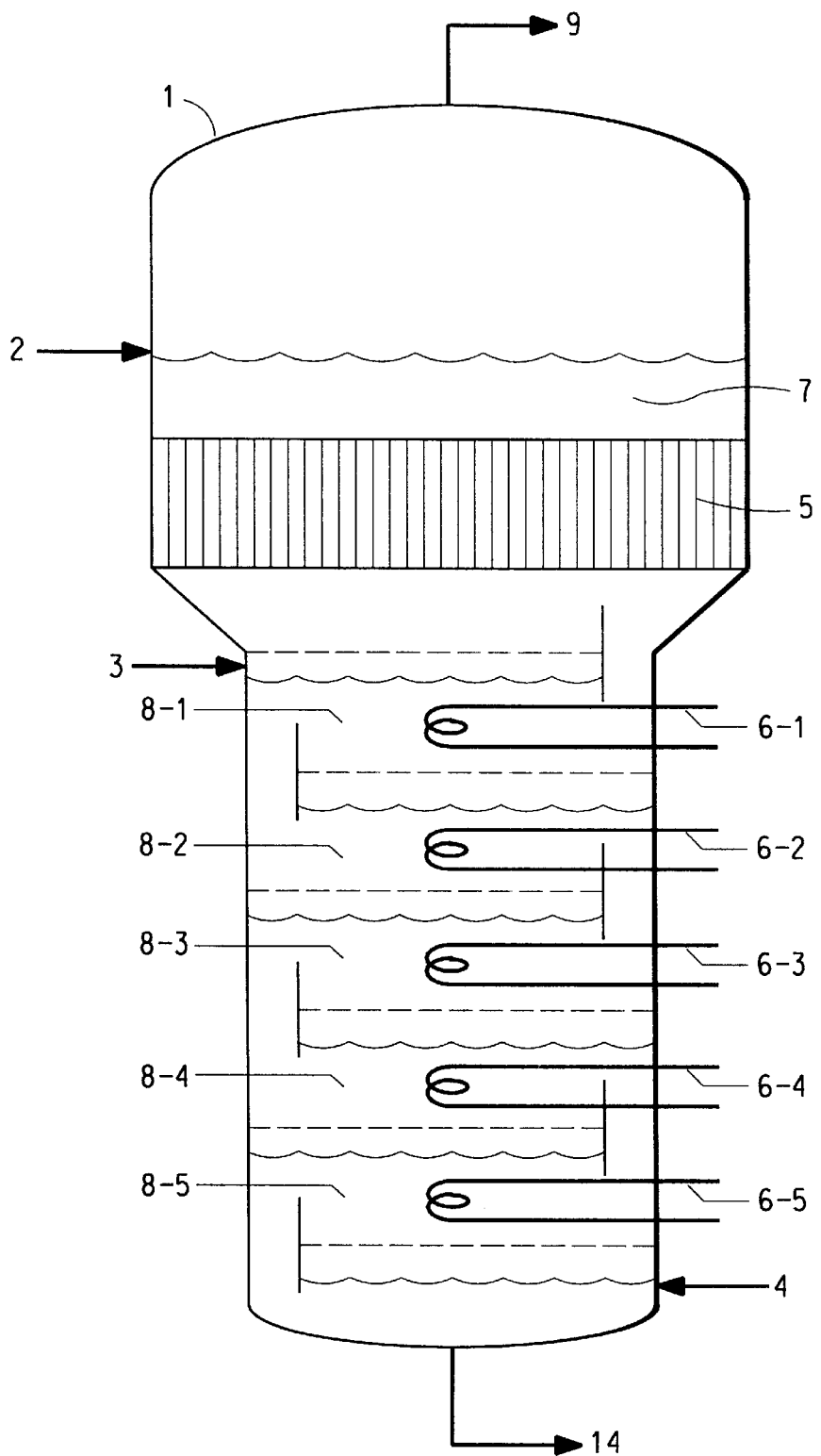
FIG. 2 is a schematic representation of the dehydration reactor utilized in a preferred embodiment of the process of the present invention.

FIG. 2 presents an expanded view of the reactor vessel (1). Features 2, 3, 4, 5, 7, 9 and 14 are identified as in FIG. 1. The five dehydration zone heaters (6-1 to 6-5) and five dehydration stages (8-1 to 8-5) are individually identified. In one preferred embodiment, the temperature gradation down the column and pressure gradient down the column is anticipated to be as in the chart below:

| Location | Temperature (° C.) | Pressure (mm Hg) |
|---|---|---|
| top (9) | 120–130 | 780 |
| evap zone (7) | 120–130 | 830 |
| 8-1 | 115 | — |
| 8-2 | 120 | — |
| 8-3 | 130 | 860 |
| 8-4 | 135 | — |
| 8-5 | 140 | — |
| below 8-5[(14)] | 145 | 920 |

EXAMPLES

Example 1

Manufacture of Isosorbide—Steady State Operation of the Reactor System of FIGS. 1 and 2

(Size of reactor approx 14 feet high, 5.5 ft diameter at lower section)

A stream of sorbitol 70% (balance water) of 6400 lbs/hr is introduced via inlet (2). Aqueous sulfuric acid, 10% by weight, is introduced at (3) in sufficient quantity to maintain its concentration at 1 weight % of the reaction mass at that point. Nitrogen (at 145° C.) is introduced at (4) in an amount of 190 lb-mol/hr. Heat input to heaters 5 and heater 6-1 through 6-5 is adjusted to maintain the thermal and pressure gradient indicated in the above table. Product stream comprising 70–80% isosorbide with the balance comprising isosorbide oligomers, decomposition products and monoanhydro sorbitol derivatives exits the reactor at outlet (14) at the rate of 3000 lbs/hr.

What is claimed is:

1. A continuous process for the preparation of a dianhydro sugar alcohol comprising the steps of:

a) introducing to the first stage of a multistage reactor a process stream comprising at least one sugar alcohol or monoanhydro sugar alcohol and optionally, water;

b) intimately contacting said process stream with a counter current flow of an inert gas at elevataed temperature to remove the bulk of any water present to yield a dewatered process stream;

c) intimately contacting said dewatered process stream with a dehydration catalyst in the presence of a counter current flow of an inert gas at elevated temperatures to remove water of reaction as formed; and d) removing the reaction product from the bottom of the reactor.

2. The process of claim 1 wherein the at least one sugar alcohol is sorbitol and the product is isosorbide.

3. The process of claim 1 wherein the dehydration catalyst is sulfuric acid.

4. The process of claim 3 wherein the concentration of sulfuric acid is 0.25 to 2.5% by weight of the reaction mass.

5. The process of claim 4 wherein the concentration of sulfuric acid is 0.5 to 1.5% by weight of the reaction mass.

6. The process of claim 1 conducted at a temperature of from 100–180° C.

7. The process of claim 6 conducted at a temperature of from 115–160° C.

8. The process of claim 7 conducted at a temperature of from 115–145° C.

9. The process of claim 1 conducted such that the hold up time in the reactor is 1–3 hours.

10. The process of claim 1 wherein the inert gas is nitrogen or carbon dioxide.

11. The process of claim 10 wherein the inert gas is nitrogen.

12. The process of claim 11 wherein the quantity of nitrogen is 0.5 to 1.5 lbs per (100%) pound of sugar alcohol or monoanhydro sugar alcohol.

* * * * *